US005650402A

United States Patent [19]

Fost et al.

[11] Patent Number: 5,650,402
[45] Date of Patent: Jul. 22, 1997

[54] PHOSPHOLIPID ANTIMICROBIAL COMPOSITIONS

[75] Inventors: Dennis L. Fost, Ridgewood; James E. Perella, Upper Saddle River, both of N.J.

[73] Assignee: Mona Industries, Inc., Paterson, N.J.

[21] Appl. No.: 488,334

[22] Filed: Jun. 7, 1995

Related U.S. Application Data

[62] Division of Ser. No. 425,723, Apr. 20, 1995, which is a continuation of Ser. No. 74,377, Jun. 11, 1993, abandoned, which is a continuation-in-part of Ser. No. 784,154, Oct. 28, 1991, abandoned.

[51] Int. Cl.$^6$ .................. A61K 31/685; A61K 31/66; C11D 3/48
[52] U.S. Cl. .................. 514/77; 510/384; 558/169; 514/114
[58] Field of Search .................. 558/169; 514/77, 514/114; 510/384

[56] References Cited

U.S. PATENT DOCUMENTS

| | | | |
|---|---|---|---|
| 3,228,829 | 1/1966 | Wolf et al. | 167/33 |
| 3,304,349 | 2/1967 | Kwan-Ting Shen | 260/920 |
| 3,699,231 | 10/1972 | Werlein et al. | 424/286 |
| 3,830,913 | 8/1974 | Harich | 424/195 |
| 3,923,870 | 12/1975 | Singer | 260/482 |
| 3,929,561 | 12/1975 | Shema et al. | 162/161 |
| 3,987,184 | 10/1976 | Foelsch | 424/273 |
| 4,172,140 | 10/1979 | Shull et al. | 424/273 |
| 4,202,882 | 5/1980 | Schwartz | 424/76 |
| 4,209,449 | 6/1980 | Mayhew et al. | 260/403 |
| 4,215,064 | 7/1980 | Lindemann et al. | 260/403 |
| 4,233,192 | 11/1980 | Lindemann et al. | 252/545 |
| 4,243,602 | 1/1981 | O'Lenick, Jr. et al. | 260/403 |
| 4,261,911 | 4/1981 | Lindemann et al. | 260/403 |
| 4,283,542 | 8/1981 | O'Lenick, Jr. et al. | 548/112 |
| 4,323,602 | 4/1982 | Parker | 427/298 |
| 4,336,385 | 6/1982 | Mayhew et al. | 548/112 |
| 4,336,386 | 6/1982 | O'Lenick, Jr. et al. | 548/112 |
| 4,380,637 | 4/1983 | Lindemann et al. | 548/112 |
| 4,454,146 | 6/1984 | Borovian | 424/270 |
| 4,496,576 | 1/1985 | Loncrini et al. | 514/389 |
| 4,503,002 | 3/1985 | Mayhew et al. | 260/945 |
| 4,655,815 | 4/1987 | Jakubowski | 71/67 |
| 4,844,891 | 7/1989 | Rosen et al. | 424/76.4 |

OTHER PUBLICATIONS

Mona Industries, Technical Bulletin, No. 905-1a, Apr. 1983.
Mona Industries, Technical Bulletin, No. 905d, Dec. 1989.

*Primary Examiner*—Johann Richter
*Assistant Examiner*—Michael G. Ambrose
*Attorney, Agent, or Firm*—Franklyn Schoenberg; Norman E. Lehrer

[57] ABSTRACT

There is provided antimicrobial agents which exhibit broad spectrum antibacterial and antifungal activity of the formula:

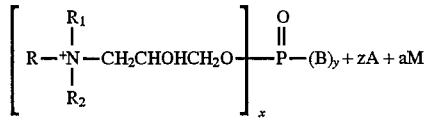

wherein:

$x=1$ to 3 or, preferably, mixtures thereof $x+y=3$ $z=x$ $a=0$ to 2

$B=O^-$ or OM $A=$Anion

M is a cation

R, $R_1$ and $R_2$ are the same or different and are alkyl, substituted alkyl, alkyl aryl or alkenyl groups of up to 16 carbon atoms with the proviso that the total carbon atoms in $R+R_1+R_2$ is between 10 and 24.

7 Claims, No Drawings

PHOSPHOLIPID ANTIMICROBIAL COMPOSITIONS

REFERENCE TO RELATED APPLICATIONS

This is a division of prior application Ser. No. 425,723, filed Apr. 20, 1995 which is a continuation of prior application Ser. No. 074,377, filed Jun. 11, 1993, now abandoned which is a continuation-in-part of application Ser. No. 784,154, filed Oct. 28, 1991, now abandoned.

FIELD OF THE INVENTION

The present invention relates to novel antimicrobial compositions and, more particularly, to a class of compounds having specific quaternized amine compounds linked to specific phosphate esters which exhibit broad spectrum bactericidal and fungicidal activity referred to hereinafter as "antimicrobial phospholipids". The phospholipid compositions of the invention are well tolerated by human tissue making them suitable for use as preservative and disinfectant components in the preparation of personal care, household cleaning and like products which exhibit enhanced antimicrobial and antifungal characteristics.

BACKGROUND OF THE INVENTION

Phosphate ester and quaternary amine compounds are well known and have been widely used for many years for a variety of applications including those requiring surfactant properties. Known phosphate esters do not generally exhibit any antimicrobial characteristics, and while quaternary amine compounds are known in general to exhibit antimicrobial activity, such compounds are extremely irritating and thus have limited usefulness in personal care and cosmetic products. More recently, various betaine-type derivatives having, in general, quaternized alkyl amine groups and at least one phosphorous-containing anion in the molecule referred to hereinafter as "synthetic phospholipids", have been disclosed and suggested as, for example, in U.S. Pat. Nos. 4,215,064; 4,233,192 and 4,380,637 to Lindemann et al., U.S. Pat. Nos. 4,209,449; 4,336,385 and 4,503,002 to Mayhew et al., and U.S. Pat. Nos. 4,243,602; 4,283,542 and 4,336,386 to O'Lenick et al. These synthetic phospholipids are suggested as exhibiting an outstanding combination of surfactant characteristics as well as being well tolerated by human tissue, i.e., they exhibit exceptionally low ocular irritation and oral toxicity. While these known phospholipids have been found useful as surfactants in a variety of personal care, household cleaning and the like products, such products also require the incorporation of antimicrobial preservatives to inhibit microbial spoilage and increase the shelf life.

It is well known that there is a need for effective preservatives in a wide variety of applications where inhibiting the growth of microorganisms is necessary, as for example, personal care products such as shampoos, creams, lotions, cosmetics, liquid soaps, and household products such as fabric cleaners and softeners, hard surface cleaners and the like. The shelf life of these preparations depends on their resistance to microbial spoilage. In addition, antimicrobial agents are a matter of substantial commercial importance in many industrial applications and products such as in paint, wood, textiles, adhesives and sealants, leather, plastics, oil, rubber and metal working fluids etc.

Certain compounds have long been known and used commercially as preservatives. For example, 1,3-dimethylol-5,5-dimethylhydantoin (DMDMH) is useful as a formaldehyde donor for the preservation of personal care products, cosmetics and household products and halopropynyl carbamates are known for their fungicidal activity. Other commercially known preservatives include Quaternium-15 (DOWICIL 200 from Dow Chemical Company); Imidazolidinyl urea (GERMALL 115 from Sutton Laboratories); formaldehyde in the free state, as in formalin; alkyl parabens (e.g. methyl, ethyl and propyl) etc. While such materials have achieved commercial acceptance for many personal care and household products, they generally present a variety of limitations for such use including being unduly expensive; exhibiting limited anti-microbial or antifungal activity, or limited solubility in water; exhibiting undue pH dependence, adverse toxicological properties and skin sensitization or possible carcinogenicity; or they may be inactivated by commonly used materials.

Various synergistic combinations of ingredients have been also suggested for use as preservatives in certain applications such as, for example, disclosed in U.S. Pat. Nos. 3,699,231; 3,929,561; 4,454,146; 4,655,815; but these compositions generally exhibit unfavorable toxicity characteristics, particularly skin and eye irritation, and are not suitable for personal care and household products, and the development of effective, inexpensive, multifunctional products having a broad spectrum activity has long been sought.

SUMMARY OF THE INVENTION

In accordance with the present invention there has now been discovered novel antimicrobial agents which surprisingly exhibit both excellent broad spectrum antibacterial and antifungal activity and are suitable for use as preservative and/or disinfectant agents in a variety of personal care compositions, household cleaning formulations and the like. The novel antimicrobial agents of the invention comprise particular synthetic phospholipid compounds that may be represented by the following general formula:

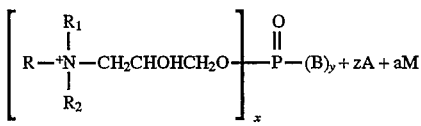

wherein:

x=1 to 3 or, preferably, mixtures thereof x+y=3 z=x a=0 to 2

B=O⁻ or OM

A=Anion

M is a cation

R, $R_1$ and $R_2$ are the same or different and are alkyl, substituted alkyl, alkyl aryl or alkenyl groups of up to 16 carbon atoms with the proviso that the total carbon atoms in R+$R_1$+$R_2$ is between 10 and 24.

It has been discovered that the particular synthetic antimicrobial phospholipids of the invention not only surprisingly and unexpectedly exhibit both broad spectrum bactericidal and fungicidal activity suitable for use as preservative and/or disinfectant agents in personal care and household products, but even small amounts of the phospholipid compositions of the invention exhibit effective antimicrobial activity and the antimicrobial phospholipid compounds of the invention are extremely well tolerated by human tissue, i.e., they exhibit exceptionally low ocular and skin irritation and oral toxicity. Moreover, they can be used in product formulations containing nonionic, anionic, amphoteric and/or cationic components without significant inhibition or reduction of the required antimicrobial activity. The antimicrobial agents of the invention may also be used in combination with other known antimicrobial agents, when desired for particular applications, to enhance the antimicrobial effectiveness thereof.

In another aspect of the invention, there is provided a method of inhibiting the growth of microorganisms in personal care, household cleaning and the like products which comprises incorporating in a personal care or household cleaning formulation an antimicrobial effective amount of an antimicrobial phospholipid compound of the general formula:

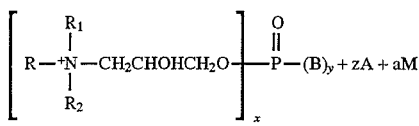

wherein:

x=1 to 3 or, preferably, mixtures thereof x+y=3 z=x a=0 to 2

B=O⁻ or OM

A=Anion

M is a cation

R, $R_1$ and $R_2$ are the same or different and are alkyl, substituted alkyl, alkyl aryl or alkenyl groups of up to 16 carbon atoms with the proviso that the total carbon atoms in $R+R_1+R_2$ is between 10 and 24.

In a still further aspect of the present invention, there is provided a personal care composition or a household cleaning composition which comprises a surface active agent and an antimicrobial effective amount of an antimicrobial phospholipid compound component of the general formula:

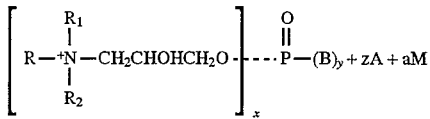

wherein:

x=1 to 3 or, preferably, mixtures thereof x+y=3 z=x a=0 to 2

B=O⁻ or OM

A=Anion

M is a cation

R, $R_1$ and $R_2$ are the same or different and are alkyl, substituted alkyl, alkyl aryl or alkenyl groups of up to 16 carbon atoms with the proviso that the total carbon atoms in $R+R_1+R_2$ is between 10 and 24.

In yet another aspect of the invention there is provided a method of preparing an antimicrobial compound which exhibits broad spectrum antibacterial and antifungal activity suitable for use as an antimicrobial agent in personal care and household products, said antimicrobial compound comprising an antimicrobial phospholipid that may be represented by the general formula:

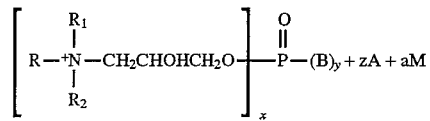

wherein:

x=1 to 3 or, preferably, mixtures thereof x+y=3 z=x a=0 to 2

B=O⁻ or OM

A=Anion

M is a cation

R, $R_1$ and $R_2$ are the same or different and are alkyl, substituted alkyl, alkyl aryl or alkenyl groups of up to 16 carbon atoms with the proviso that the total carbon atoms in $R+R_1+R_2$ is between 10 and 24.

which comprises:

reacting a phosphate ester reactant with a tertiary amine in the molar ratio of from 1:1 to 3:1, and preferably from at least 2.0:1, of amine to phosphate ester until the tertiary amine is completely reacted, said phosphate ester reactant being of the general formula:

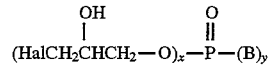

wherein:

x=1 to 3 or, preferably, mixtures thereof x+y=3

B=O⁻ or OM

Hal=halogen and said tertiary amine being of the general formula:

wherein R, $R_1$ and $R_2$ is the same or different and are alkyl, substituted alkyl, alkyl aryl or alkenyl groups of up to 16 carbon atoms with the proviso that the total carbon atoms in $R+R_1+R_2$ is between 10 and 24.

As used herein the phrases "antimicrobial" and "inhibiting microbial growth" describes the killing of, as well as the inhibition or control of the growth of bacteria (gram positive and gram negative), fungi, yeasts and molds.

DETAILED DESCRIPTION OF THE INVENTION

The present invention is directed to novel antimicrobial agents which surprisingly and unexpectedly exhibit excellent broad spectrum bactericidal and fungicidal activity and effectiveness and effectively inhibit the growth of a variety of bacteria, yeast and molds. Moreover, such active agents may be used in combination with or in the presence of anionic, nonionic, amphoteric and/or cationic surfactants without inhibition of the antimicrobial efficacy thereof and are virtually non-irritating to the skin and eyes; thus, such antimicrobial agents may be used in diverse formulations and applications.

The novel antimicrobial agents of the present invention comprise a class of synthetic "antimicrobial phospholipid" compounds which may be represented by the following general formula:

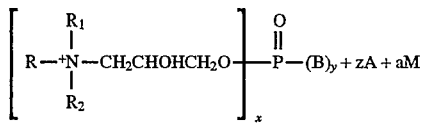

wherein:

x=1 to 3 or, preferably, mixtures thereof x+y=3 z=x a=0 to 2

B=O$^-$ $^{OM}$

A=Anion

M is a cation

R, $R_1$ and $R_2$ are the same or different and are alkyl, substituted alkyl, alkyl aryl or alkenyl groups of up to 16 carbon atoms with the proviso that the total carbon atoms in R+$R_1$+$R_2$ is between 10 and 24.

The antimicrobial phospholipid compounds described which, as indicated, exhibit broad spectrum antimicrobial activity as well as being substantially non-irritating to humans can be prepared by reaction of tertiary amines and phosphate esters corresponding to the amine and phosphate ester moieties in the above formula. Such compounds can be prepared by reacting the corresponding tertiary amine and phosphate ester reactants in the molar ratio of 1:1 to 3:1, and preferably from at least about 2.5:1 of amine to phosphate ester, for the time necessary for the amine to be completely reacted.

Tertiary amines suitable for use in accordance with the practice of the invention can be represented by the general formula:

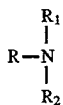

wherein R, $R_1$ and $R_2$ is the same or different and are alkyl, substituted alkyl, alkyl aryl, or alkenyl groups of up to 16 carbon atoms with the proviso that the total carbon atoms in R+$R_1$+$R_2$ is between 10 and 24.

Exemplary tertiary amines include:

tributylamine (di(hydroxyethyl)hexyl)-amine bis(2-hydroxyethyl)cocoamine

N,N-dimethyl-dodecylamine

N,N-dimethyl-tetradecylamine

N,N-dimethyl-hexadecylamine

N,N-dimethyl-cocoamine

N,N-dimethyl-cetylamine dimethyl ($C_8$–$C_{16}$) alkyl amine

The phosphate ester reactants suitable for use in accordance with the practice of the invention can be represented by the general formula:

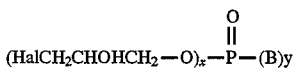

wherein:

x=1 to 3 or, preferably, mixtures thereof x+y=3

B=O- or OM

Hal-halogen

The phosphate ester intermediate may be prepared by known procedures wherein phosphoric acid and various phosphate salts, and preferably monosodium phosphate, are reacted in an aqueous medium with epichlorohydrin, generally in the molar ratio of about 1:3, until the reaction is complete.

As noted, the instant invention is based upon the discovery that the antimicrobial compounds of the invention described above are effective in controlling the growth of bacteria, yeasts and molds in diverse formulations and applications such as cosmetic, toiletries, personal care, household and related products and materials. The antimicrobial agents ok the invention are not only an effective antimicrobial for the destruction or control of fungi and bacteria that cause degradation and deterioration of diverse personal care and household product formulations, but also by their activity against the organisms that can reside and accumulate on various surfaces, can provide utility in sanitizing, disinfecting and bacteriostatic applications.

The antimicrobial activity of the compounds described above has been confirmed using standard laboratory techniques, including the Minimum Inhibitory Concentration (MIC) technique. They have been found effective, for example, in inhibiting bacteria including *S. aureus, E. coli, P. aeruginosa* and *S. choleraesuis*. They have also been found effective against yeast and mold including *C. albicans* and *A. niger*. In these tests it has been determined that the presence of anionic, nonionic, amphoteric and/or cationic materials did not inhibit the antimicrobial efficacy nor did a variety of inactivators commonly encountered in personal care and household applications. The broad spectrum preservative characteristics of the antimicrobial phospholipids of the invention in typical cosmetic formulations have also been established and confirmed.

Specifically, molds and yeasts which may be inhibited include *Aspergillus niger, Candida albicans* plus various species of Penicillium, Tricholphyton, Alternaria, Gliocladium, Paecilomyces, Mucor, Fusarium, Geotrichum, Cladosporium and Trichoderma. Examples of the bacteria include *Salmonella choleraesuis, Serratia marcescens, Klebsiella pneumoniae, Enterobacter aerogenes, Aerobacter aerogenes, Proteus vulgaris, Streptococcus faecalis, Pseudomonas aeruginosa, Escherichia coli, Staphylococcus aureus, Staphylococcus epidermidis, M. luteus, P. mirabilis, P. cepacia, P. stutzeri* and *A. hydrophilia*.

Another aspect of the present invention is the discovery that the antimicrobial phospholipid compounds surprisingly and unexpectedly exhibit significant spermicidal and antiviral activity which further enhances the utility of the compounds of the invention for a diversity of applications.

The antimicrobial phospholipid compounds described above have activity against bacteria, yeasts and molds when employed at appropriate levels of concentration and may be used to inhibit growth or effectively destroy these organisms. It should be obvious that the required effective concentration or amount will vary with particular organisms and also on a number of other factors in particular applications.

In general, however, effective antimicrobial response is obtained when the active agent is employed in concentrations ranging between 5 and 10,000 ppm (parts per million) and preferably between about 50 and 1,000 ppm. Generally, the concentration of the agent required for bactericidal activity will be lower than the concentration required for fungicidal activity.

For other applications, amounts of from 0.04% to about 5% or higher, and preferably from 0.07% to about 3.0, by weight of the active agent of the present invention is incorporated into a composition or sprayed onto or otherwise applied to a substrate to be treated in order to prevent growth of bacteria, yeasts and molds. It will also be understood that the antimicrobial agents of the invention may be used in combination with other antimicrobial materials.

The compatibility of the antimicrobial phospholipid compounds of the invention with human tissue, i.e., dermal and eye tissue has also been tested. In these tests, 48-hour human patch dermal evaluations (5% in water), in vitro ocular evaluations (3% in water) and repeated insult patch tests (3% in water) determined that the compounds are substantially non-irritating to humans, they are safe and suitable for use in eye area products and are not a skin sensitizer to humans.

The antimicrobial phospholipid compounds of the invention may be incorporated in diverse personal care and household product formulations as, for example, a preservative therefore and/or as a disinfectant agent, and the incorporation of the compounds of the invention into such products can be done in accordance with standard practices.

The invention will now be further illustrated by reference to certain specific examples which are provided herein for purposes of illustration only and are not intended to limit the scope therein.

EXAMPLE 1

925.6 grams of soft water are charged to a reaction vessel and heat is applied to 50° C. 554.4 grams of dimethyl cocoamine ($C_{12}$-66%; $C_{14}$-26%; C16-8%) are charged into the reaction vessel under good agitation and heat is applied to 90° C. An aqueous solution of 938.8 grams of 40% active 3-chloro-2-hydroxy-propylphosphate (3:1) are charged into the reaction vessel in 4 equal icrements over 1.5 hours using good agitation while maintaining the temperature at 90°–95° C. Heating is continued at 90°–95° C. until the pH (10%) is 6.5 or less and the percentage of free tertiary amine is 0.5% maximum; approximately 6 to 9 hours. The reaction mixture is then cooled to 80° C., 55.2 grams of 50% NaOH are charged into the reaction vessel and the reaction mixture is heated back to 90° C. Heating at 90° C. is continued until the percentage of NaCl is 6.9±0.2%, approximately 1 hour. The reaction mixture is then cooled to 50° C. and the pH (10%) is adjusted to 7.0±0.5 with citric acid (approximately 9.7 grams). 22.1 grams of $H_2O_2$ (35%) are charged to the reaction vessel with good agitation and heat is applied to 90° C. and maintained for 1 hour. The reaction mixture is then cooled to 50° C. and discharged. The product is a clear liquid having ≤0.5% free amine, a pH (10%) of 7.0±0.5 and a specific gravity @25° C. of 1.05.

EXAMPLE 2

682.4 grams of propylene glycol and 453.0 grams of water are charged to a reaction vessel and heat is applied to 50° C. 655.2 grams of dimethyl cetylamine are charged into the reaction vessel with good agitation and heat is applied to 90° C. An aqueous solution of 938.8 grams of 40% active 3-chloro-2-hydroxy-propylphosphate (3:1) are divided into 4 equal increments and charged into the reaction vessel over 1.5 hours while maintaining the temperature at 90°–95° C. Heating is continued at 90°–95° C. until the pH (10%) is 6.5 or less and the free tertiary amine is ≤0.5%, approximately 6 to 9 hours. The reaction mixture is then cooled to 80° C. and 47.3 grams of 50% NaOH is added with good agitation. Heat is applied to 90° C. and maintained until the percentage of NaCl is 6.1±0.2%, approximately 1 hour. The reaction mixture is then cooled to 50° C. and the pH (10%) is adjusted to 7.0±0.5 with citric acid, approximately 4.7 grams being added. 25 grams of 35% $H_2O_2$ are charged into the reaction vessel, heat is applied to 90° C. and maintained for 1 hour. Reaction mixture is then cooled to 50° C. and discharged.

The product is a clear liquid having a specific gravity @25° C. of 1.05, a pH (10%) of 7.0±0.5 and Free amine of ≤0.5%.

EXAMPLE 3

A synthetic phospholipid such as disclosed in U.S. Pat. No. 4,209,449 is prepared for comparison with the antimicrobial phospholipid compositions of the present invention.

To 885.4 gms of deionized water charged to a reaction vessel, 038.8 gms of 3-chloro-2-hydroxy-propylphosphate (3:1) are added under good agitation while heating to 50°–55° C., and then 873 gms of cocoamidopropyl dimethyl amine are charged into the reaction vessel under good agitation. After the amido amine is charged, the reactor is heated to 90°–95° C. and when batch reaches 90°–95° C., it is held under reflux for 2 to 5 hours until inorganic chloride reaches theoretical values (6.5%). The reaction mixture is then cooled to 30° C. and discharged.

The product is a clear liquid having a specific gravity @25° C. of 1.1 and a pH at 10% of 6.0–7.5.

EXAMPLE 4

Products such as prepared in Example 1 and Example 2 are screened for antimicrobial activity using a modified Minimum Inhibitory Concentration (MIC) testing protocol. The initial screening is conducted using the following test organisms:

*Staphylococcus aureus* ATCC #6538
*Candida albicans* ATCC #10259
*Aspergillus niger* ATCC #6275
*Penicillium variable* ATCC #XXXX The growth media used are Brain Heart Infusion Broth for bacteria and Sabouroud Broth for yeast and mold.

A series of ten sequential two-fold dilutions of the test material is made in an appropriate growth promoting culture medium for each organism to be tested. A standard number of microorganisms are inoculated into each of the prepared dilutions containing the medium plus the test material. Inoculated tubes are incubated at appropriate temperature for 72 hours.

Visual readings are taken after 24, 48 and 72 hours. The 72-hour incubated tubes are subcultured on agar media to verify inhibition of growth. Data is recorded as positive or negative for growth at each of the dilutions of the test material under evaluation. The minimum lethal concentration is defined as the smallest concentration of antimicrobial agent that, on subculture, either fails to show growth or results in a 99.9% decrease in the initial concentration of inoculum.

Comparative MIC data of the initial screening test is reported in Table I.

TABLE I

| Test Organism | Example I Type Sample | Example II Type Sample |
|---|---|---|
| S. aureus | 20 ppm | 60 ppm |
| C. Albicans | 20 ppm | 80 ppm |
| A. niger | 10 ppm | 30 ppm |
| P. variable | 10 ppm | 80 ppm |

An additional test panel is conducted to evaluate products such as prepared in Example 1 and Example 2. The further tests are conducted with *Pseudomonas aeruginosa* ATCC #15442, *Escherichia coli* ATCC #8739 and *Salmonella choleraesuis* ATCC #10708. The MIC test protocol described above is used in conducting the additional test.

Comparative MIC data of the additional screening test is reported in Table II.

TABLE II

| Test Organism | Example I Type | Example 2 Type |
|---|---|---|
| P. aerugenosa | 80 ppm | 80 ppm |
| E. coli | 20 ppm | 160 ppm |
| S. choleraesuis | 20 ppm | 80 ppm |

As can be seen, both the Example 1 and Example 2 type of products exhibit significant antimicrobial properties.

For comparison, products such as prepared in Example 3 are screened for antimicrobial activity using the modified minimum Inhibitory Concentration (MIC) testing protocol described above. Comparative MIC data of the screening tests are reported in Table III.

TABLE III

| Test Organism | MIC (ppm) |
|---|---|
| *Staphylococcus aureus* (#6538) | 300 |
| *Escherichia coli* (#8739) | 50 |
| *Pseudomonas aeruginosa* (#15442) | 300 |
| *Salmonella choleraesuis* (#10708) | 1250 |
| *Enterobacter aerogenes* (#13048) | 1250 |
| *Klebsiella pneumoniae* (#13883) | 1250 |
| *Candida albicans* (#10259) | 50 |
| *Aspergillus niger* (#6275) | 625 |
| *Penicillium expansum* (#1117) | 75 |
| *Aspergillus oryzae* (#10196) | 5000 |

The overall exceptional range of antimicrobial activity by products such as those prepared in Examples 1 and 2 against a variety of bacterial and fungal microorganisms in the order of 10 to 160 ppm with a usual effectiveness level of less than 100 ppm is substantially greater than the general antimicrobial activity of products such as prepared in Example 3, as would be evident from the test results reported in Table III.

EXAMPLE 5

A series of typical personal care products are prepared by standard practices using the following proportion of ingredients:

Product A

Shampoo

| | |
|---|---|
| Sodium Lauryl Sulfate | 15.0% by weight |
| Water | 85.0% |
| Antimicrobial Phospholipid (Example 1 Type) | variable |

Compositions are prepared with the following proportions of the product of the Example 1 type.

| Test Sample | Example 1 Type Product |
|---|---|
| A-1 | 0.00% by weight |
| A-2 | 0.25% by weight |
| A-3 | 0.50% by weight |
| A-4 | 1.0% by weight |

Product B

Make-Up Foundation

| | | |
|---|---|---|
| a) Steareth - 20 | | 1.5% by weight |
| Pigment | | 15.0% by weight |
| 0.5% Kelzan AR/1% NaCl | | 76.0% by weight |
| b) Steareth - 2 | | 2.5% by weight |
| Isopropyl Myristate | | 2.0% by weight |
| Hexyl Laurate | | 2.0% by weight |
| Dow Fluid 200/100 cs | | 1.0% by weight |
| Antimicrobial Phospholipid | | variable |
| Pigment: | White | 13.5% by weight |
| | Red | 0.15% by weight |
| | Brown | 1.20% by weight |
| | Yellow | 0.15% by weight |

Compositions are prepared with the following proportions of the product of the Example 1 type.

| Test Sample | Example 1 Type Product |
|---|---|
| B-1 | 0.00% by weight |
| B-2 | 0.25% by weight |
| B-3 | 0.50% by weight |
| B-4 | 1.0% by weight |

Product C

Lotion

| | |
|---|---|
| a) Steareth - 20 | 2.0% by weight |
| Water | 87.5% by weight |
| Product of Example 1 | variable |
| b) Steareth - 2 | 3.0% by weight |
| Isopropyl Myristate | 5.0% by weight |
| Cetearyl Alcohol | 2.5% by weight |

Compositions are prepared with the following proportions of the product of the Example 1 type.

| Test Sample | Example 1 Type Product |
|---|---|
| C-1 | 0.0% by weight |
| C-2 | 0.1% by weight |
| C-3 | 0.5% by weight |

EXAMPLE 6

The personal care products of Example 5 are subject to Preservative Challenge Tests as follows:

Aliquots of each test preparation are inoculated with separate representative mixed cultures of bacteria and fungi. Plate counts to determine survivors are performed at 0 time and after 3, 7, 14, 21 and 28 days of incubation. Bacterial samples showing a less than 10 recovery at 14 days are re-inoculated at 21 days. Results are presented as surviving organisms present at each time interval per gram of product tested.

Product A
INOCULUM
a) Mixed bacteria: *Pseud. aeruginosa* (ATCC 15442); *E. coli* (ATCC 8739 or 11229); *S. aureus* (ATCC 6536).
b) Mixed fungi: *A. niger* (ATCC 9642); *P. luteum* (ATCC 9644); *C. albicans* (ATCC 10231).

| TEST SAMPLE | DAYS | BACTERIA | FUNGI | CONTROL |
|---|---|---|---|---|
| A-1 | 0 | 2,100,000 | 740,000 | <10 |
|  | 3 | 17,500 | 4,750 | <10 |
|  | 7 | 2,100,000 | 740,000 | <10 |
|  | 14 | 2,100,000 | 740,000 | <10 |
|  | 21* | 2,100,000 | 740,000 | <10 |
|  | 28 | 2,100,000 | 740,000 | <10 |
| A-2 | 0 | 2,100,000 | 740,000 | <10 |
|  | 3 | 24,200 | 1,900 | <10 |
|  | 7 | <10 | <10 | <10 |
|  | 14 | <10 | <10 | <10 |
|  | 21* | <10 | <10 | <10 |
|  | 28 | <10 | <10 | <10 |
| A-3 | 0 | 2,100,000 | 740,000 | <10 |
|  | 3 | 16,900 | 9,700 | <10 |
|  | 7 | <10 | <10 | <10 |
|  | 14 | <10 | <10 | <10 |
|  | 21* | <10 | <10 | <10 |
|  | 28 | <10 | <10 | <10 |
| A-4 | 0 | 2,100,000 | 740,000 | <10 |
|  | 3 | 23,700 | 1,620 | <10 |
|  | 7 | <10 | <10 | <10 |
|  | 14 | <10 | <10 | <10 |
|  | 21* | <10 | <10 | <10 |
|  | 28 | <10 | <10 | <10 |

*21-day Re-inoculation
NOTE:
Control is an uninoculated sample for background count.
Bacterial and Fungal Counts are as organisms recovered per gram of sample.
Test Day is the number of days after inoculation of the test sample.

As can be seen, the antimicrobial product of the Example #1 type is highly effective against both bacterial and fungal challenges at a concentration of 0.25%. Moreover, the antimicrobial product of the Example #1 type is not adversely affected by anionics such as Na Lauryl Sulfate.

Product B
INOCULUM
a) Mixed bacteria: *Pseud. aeruginosa* (ATCC 15442); *E. coli* (ATCC 8739 or 11229); *S. aureus* (ATCC 6536).
b) Mixed fungi: *A. niger* (ATCC 9642); *P. luteum* (ATCC 9644); *C. albicans* (ATCC 10231).

| TEST SAMPLE | DAYS | BACTERIA | FUNGI | CONTROL |
|---|---|---|---|---|
| B-1 | 0 | 2,100,000 | 740,000 | <10 |
|  | 3 | 2,100,000 | 740,000 | <10 |
|  | 7 | 2,100,000 | 740,000 | <10 |
|  | 14 | 2,100,000 | 740,000 | <10 |
|  | 21* | 2,100,000 | 740,000 | <10 |
|  | 28 | 2,100,000 | 740,000 | <10 |
| B-2 | 0 | 1,980,000 | 750,000 | <10 |
|  | 3 | 57,000 | 4,200 | <10 |
|  | 7 | <10 | 120 | <10 |
|  | 14 | <10 | 1,420 | <10 |
|  | 21* | <10 | 5,300 | <10 |
|  | 28 | <10 | 7,400 | <10 |
| B-3 | 0 | 2,100,000 | 740,000 | <10 |
|  | 3 | 12,000 | 3,400 | <10 |
|  | 7 | <10 | <10 | <10 |
|  | 14 | <10 | <10 | <10 |
|  | 21* | <10 | <10 | <10 |
|  | 28 | <10 | <10 | <10 |
| B-4 | 0 | 2,100,000 | 700.000 | <10 |
|  | 3 | 3,000 | <10 | <10 |
|  | 7 | <10 | <10 | <10 |
|  | 14 | <10 | <10 | <10 |
|  | 21* | <10 | <10 | <10 |
|  | 28 | <10 | <10 | <10 |

*21-day Re-inoculation
NOTE:
Control is an uninoculated sample for background count.
Bacterial and Fungal Counts are as organisms recovered per gram of sample.
Test Day is the number of days after inoculation of the test sample.

As can be seen, the antimicrobial product of the Example #1 type is highly effective against both bacterial and fungal challenges at a concentration of 0.50%. At 0.25%, the product of the Example #1 type is effective against the bacterial inoculum but failed to completely eradicate the fungi after initial reductions were noted.

Product C
INOCULUM
a) Mixed bacteria: *Pseud. aeruginosa* (ATCC 15442); *E. coli* (ATCC 8739 or 11229); *S. aureus* (ATCC 6536).
b) Mixed fungi: *A. niger* (ATCC 9642); *P. luteum* (ATCC 9644); *C. albicans* (ATCC 10231).

| TEST SAMPLE | DAYS | BACTERIA | FUNGI | CONTROL (Uninoculated) |
|---|---|---|---|---|
| C-1 | 0 | 2,100,000 | 310,000 | 610 |
|  | 3 | 2,700,000 | 350,000 | 1,220 |
|  | 7 | TNTC* | TNTC | TNTC |
|  | 14 | TNTC | TNTC | TNTC |
|  | 21 | TNTC | TNTC | TNTC |
|  | 28 | TNTC | TNTC | TNTC |
| *TNTC - Too Numerous to Count | | | | |
| C-2 | 0 | 2,400,000 | 250,000 | <10 |
|  | 3 | <10 | 6,340 | <10 |
|  | 7 | <10 | 5,100 | <10 |
|  | 14 | <10 | 1,260 | <10 |
|  | 21* | <10 | 2,140 | <10 |
|  | 28 | <10 | 2,970 | <10 |
| C-3 | 0 | 1,900,000 | 290,000 | <10 |
|  | 3 | <10 | 2,170 | <10 |
|  | 7 | <10 | <10 | <10 |
|  | 14 | <10 | <10 | <10 |

| | Product C INOCULUM |
|---|---|
| | a) Mixed bacteria: *Pseud. aeruginosa* (ATCC 15442); *E. coli* (ATCC 8739 or 11229); *S. aureus* (ATCC 6536). b) Mixed fungi: *A. niger* (ATCC 9642); *P. luteum* (ATCC 9644); *C. albicans* (ATCC 10231). |

| TEST SAMPLE | DAYS | BACTERIA | FUNGI | CONTROL (Uninoculated) |
|---|---|---|---|---|
| | 21* | <10 | <10 | <10 |
| | 28 | <10 | <10 | <10 |

*21-day Re-inoculation
NOTE:
Control is an uninoculated sample for background count.
Bacterial and Fungal Counts are as organisms recovered per gram of sample.
Test Day is the number of days after inoculation of the test sample.

As can be seen, Test sample C-3 (0.5% Product of the Example #1 type) is found to effectively eliminate both bacterial and fungal challenges within seven days of inoculation. The product of the Example #1 type at 0.5% is capable of functioning effectively as a preservative as measured by the above test parameters.

The antimicrobial test results clearly show the effectiveness of these products in preserving these systems. Noteworthy is the fact that the product of the Example #1 type is not affected by anionics such as sodium lauryl sulfate.

Having now fully described the invention, it will be apparent to one of ordinary skill in the art that many changes and modifications can be made thereto without departing from the spirit or scope of invention as set forth herein.

EXAMPLE 7

1165.8 grams of soft water are charged to a reaction vessel and heat is applied to 50° C. 693 grams of dimethyl cocoamine ($C_{12}$-66%; $C_{14}$-26%; $C_{16}$-8%) are charged into the reaction vessel under good agitation and heat is applied to 90° C. An aqueous solution of 938.8 grams of 40% active 3-chloro-2-hydroxy-propylphosphate (3:1) are charged into the reaction vessel in 4 equal increments over 1.5 hours using good agitation while maintaining the temperature at 90°–95° C. Heating is continued at 90°–95° C. until the pH (10%) is 6.5 or less and the percentage of free tertiary amine is 0.5% maximum; approximately 6 to 9 hours. The reaction mixture is then cooled to 80° C., 55.2 grams of 50% NaOH are charged into the reaction vessel and the reaction mixture is heated back to 90° C. Heating at 90° C. is continued until the percentage of NaCl is 6.9±0.2%, approximately 1 hour. The reaction mixture is then cooled to 50° C. and the pH (10%) is adjusted to 7.0±0.5 with citric acid (approximately 9.7 grams). 22.1 grams of $H_2O_2$ (35%) are charged to the reaction vessel with good agitation and heat is applied to 90° C. and maintained for 1 hour. The reaction mixture is then cooled to 50° C. and discharged. The product is a clear liquid having <0.5% free amine, a pH (10%) of 7.0±0.5 and a specific gravity @25° C. of 1.05.

EXAMPLE 8

807.1 grams of propylene glycol and 587.5 grams of water are charged to a reaction vessel and heat is applied to 50° C. 819 grams of dimethyl cetylamine are charged into the reaction vessel with good agitation and heat is applied to 90° C. An aqueous solution of 938.8 grams of 40% active 3-chloro-2-hydroxy-propylphosphate (3:1) is charged into the reaction vessel dropwise over 1.5 hours while maintaining the temperature at 90°–95° C. Heating is continued at 90°–95° C. until the pH (10%) is 6.5 or less and the free tertiary amine is <0.5%, approximately 6 to 9 hours. The reaction mixture is then cooled to 80° C. and 47.3 grams of 50% NaOH is added with good agitation. Heat is applied to 90° C. and maintained until the percentage of NaCl is 6.1±0.2%, approximately 1 hour. The reaction mixture is then cooled to 50° C. and the pH (10%) is adjusted to 7.0±0.5 with citric acid, approximately 4.7 grams being added. 25 grams of 35% $H_2O_2$ are charged into the reaction vessel, heat is applied to 90° C. and maintained for 1 hour. The reaction mixture is then cooled to 50° C. and discharged.

EXAMPLE 9

807.1 grams of propylene glycol and 587.5 grams of water are charged to a reaction vessel and heat is applied to 50° C. 819 grams of dimethyl cetylamine are charged into the reaction vessel with good agitation and heat is applied to 90° C. An aqueous solution of 938.8 grams of 40% active 3-chloro-2-hydroxy-propylphosphate (3:1) is charged into the reaction vessel while maintaining the temperature at 90°–95° C. and heating is continued at 90°–95° C. until the pH (10%) is 6.5 or less and the free tertiary amine is <0.5%, approximately 6 to 9 hours. The reaction mixture is then cooled to 80° C. and 47.3 grams of 50% NaOH is added with good agitation. Heat is applied to 90° C. and maintained until the percentage of NaCl is 6.1±0.2%, approximately 1 hour. The reaction mixture is then cooled to 50° C. and the pH (10%) is adjusted to 7.0±0.5 with citric acid, approximately 4.7 grams being added. 25 grams of 35% $H_2O_2$ are charged into the reaction vessel, heat is applied to 90° C. and maintained for 1 hour. The reaction mixture is then cooled to 50° C. and discharged.

EXAMPLE 10

Products such as prepared in Examples 7, 8 and 9 are screened for antimicrobial activity using a modified Minimum Inhibitory Concentration (MIC) testing protocol such as described in Example 4, the screening is conducted using the following test organisms:

Test Organisms
*Staphylococcus epidermidis*
*Eshcerichia coli*
*Pseudomonas aeruginose*
*Candida albicans*
*Aspergillus niger*

Comparative MIC data of the screening tests are reported in Table IV.

TABLE IV

| Test Organism | Example 7 Type | Example 8 Type | Example 9 Type |
|---|---|---|---|
| *S. epidermidis* | <40 ppm | <40 ppm | <40 ppm |
| *E. coli* | <40 ppm | <40 ppm | <40 ppm |
| *P. aerugenosa* | 80 ppm | 312 ppm | 625 ppm |
| *C. albicans* | <40 ppm | <40 ppm | <40 ppm |
| *A. niger* | <40 ppm | <30 ppm | <40 ppm |

The overall exceptional range of antimicrobial activity of products such as prepared in Examples 7, 8 and 9 against a variety of bacterial and fungal microorganisms is shown by the data in Table IV.

What is claimed is:
1. Antimicrobial compositions which exhibit broad spectrum antibacterial and antifungal activity that comprises a mixture of mono-, di- and triesters of phosphoric acid of the formula:

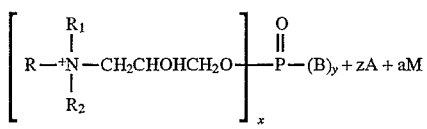

wherein:

x=1, 2 or 3;

x+y=3;

z=x;

a=0 to 2;

B=O⁻ or OM;

A=Anion;

M is a cation;

R, R₁ and R₂ are the same or different and are alkyl, substituted alkyl, alkylaryl or alkenyl groups of up to 16 carbon atoms with the proviso that the total carbon atoms in R+R₁+R₂ is between 10 and 24.

2. Antimicrobial agents as claimed in claim 1, wherein R₁ and R₂ are the same or different alkyl of 1 to 3 carbon atoms.

3. Antimicrobial agents as claimed in claim 2, wherein R is alkyl, substituted alkyl or an alkenyl group of 10 to 20 carbon atoms.

4. Antimicrobial agents as claimed in claim 1 which are preservative agents adaptable for use in a personal care composition.

5. Antimicrobial agents as claimed in claim 1 which are disinfectant agents adaptable for use in a cleaning composition.

6. Personal care and household cleaning compositions which comprise as one component thereof at least an antimicrobially effective amount of an antimicrobial composition component that consists essentially of a mixture of mono-, di- and triesters of phosphoric acid of the general formula:

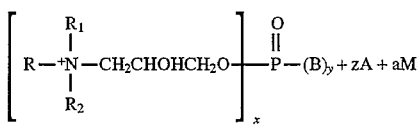

wherein:

x=1, 2 or 3 x+y=3;

z=x;

a=0 to 2;

B=O⁻ or OM;

A=Anion;

M is a cation;

R, R₁ and R₂ are the same or different and are alkyl, substituted alkyl, alkyl aryl or alkenyl groups of up to 16 carbon atoms with the proviso that the total carbon atoms in R+R₁+R₂ is between 10 and 24.

7. Personal care and household cleaning compositions as claimed in claim 6, wherein said antimicrobial composition component is a preservative.

* * * * *